United States Patent [19]

Frederick

[11] Patent Number: 4,651,732
[45] Date of Patent: Mar. 24, 1987

[54] THREE-DIMENSIONAL LIGHT GUIDANCE SYSTEM FOR INVASIVE PROCEDURES

[76] Inventor: Philip R. Frederick, 632 - 17th Ave., Salt Lake City, Utah 84143

[21] Appl. No.: 722,414

[22] Filed: Apr. 11, 1985

Related U.S. Application Data

[63] Continuation of Ser. No. 476,049, Mar. 17, 1983, abandoned.

[51] Int. Cl.⁴ .............................................. A61B 17/00
[52] U.S. Cl. ................................................. 128/303 R
[58] Field of Search ................ 128/303 R, 303.1, 305, 128/395–398, 633, 790; 219/121 LA, 121 LV, 121 LS; 604/20, 22; 362/259, 269, 275, 285, 804, 285, 287, 371, 413, 414, 418

[56] References Cited

U.S. PATENT DOCUMENTS

| | | | |
|---|---|---|---|
| 1,123,757 | 1/1915 | Knerr | 362/287 |
| 2,932,296 | 4/1960 | Sanders | 128/305 |
| 3,796,220 | 3/1974 | Bredemeier | 128/395 |
| 3,892,488 | 7/1975 | Edmonds | 219/121 LS |
| 4,092,147 | 2/1978 | Hett | 128/395 |
| 4,215,694 | 8/1980 | Isakov et al. | 128/303.1 |
| 4,273,127 | 6/1981 | Auth et al. | 128/303.1 |
| 4,289,378 | 9/1981 | Remy et al. | 128/303.1 |
| 4,337,502 | 6/1982 | Lescrenier | 362/259 |

Primary Examiner—Edward M. Coven
Assistant Examiner—Max F. Hindenburg
Attorney, Agent, or Firm—Thorpe, North & Western

[57] ABSTRACT

A three dimensional guidance system for percutaneous invasive procedures which develops a line of light above a patient's body to indicate the entry point and path of the invasive instrument. Guidance is provided by alignment of the instrument with the line of light. The line is developed at the intersection of narrow beams of light from light sources mounted at one end and one side of the patient's body. The light sources are mounted for rotation about mutually perpendicular axes and means is provided for precise adjustment of each light source relative to the patient's body to accurately position the line of intersection.

1 Claim, 4 Drawing Figures

THREE-DIMENSIONAL LIGHT GUIDANCE SYSTEM FOR INVASIVE PROCEDURES

This application is a continuation, of application Ser. No. 476,049, filed 3/17/83.

BACKGROUND OF THE INVENTION

The present invention relates to a three-dimensional light system for guidance of invasive procedures with computed tomagraphic assisted instrument placement.

Prior to the development of computed tomography (C.T.) a variety of invasive procedures, such as tissue sampling, abcess drainage, etc., had been developed as alternatives to surgery where the lesion or target could be visualized fluoroscopically. These procedures generally involved a needle puncture and were applicable to lesions of lungs and bones where the natural contrast afforded good fluoroscopic visualization.

With the development of body computed tomography, the excellent portrayal of anatomic detail and tissue delineation in computed tomographic images permitted extension of the percutaneous techniques to various parts of the body, such as the abdomen, brain and other soft tissues.

With C.T. assisted instrument placement, the patient is removed from the C.T. gantry prior to undertaking the percutaneous procedures. Therefore, the scanners include narrow, accurate light beams for relating structures visualized in the computed tomographic cross-section images to the overlying body surface by reference to these mid-line and image slice level indicators. In the most common technique of referencing, a grid giving mid-line localization is displayed on the C.T. image. Lesion depth and distance from the mid-line are noted. The patient is positioned in the gantry at this slice level and the mid-line and transverse planes are marked on the patient's skin. The table is then withdrawn from the gantry and a skin mark is made at the slice level and at a distance from the mid-line selected as the entry point. From this point, a line gives direct access to the lesion if the estimated degree of angulation is correct. Rigid guides have been developed to improve precision of instrument placement in cranial and abdominal biopsies. These devices provide precise positioning of the biopsy needle. In the abdomen they restrict the biopsy path to a plane perpendicular to the axis of rotation of the gantry but allow for precise needle angulation within this plane. The disadvantage of restricting the needle position to the plane of the image is apparent and the use of trigonometric calculations has been proposed to permit longitudinal angulation in order to avoid structures overlying the target. This technique involves selection of the point of needle insertion, computation of the distance and path to the lesion and calculation of the exact angle of needle insertion. The needle is then inserted parallel to a straight edge held adjacent to the patient at the calculated angle.

The prior art techniques are useful, but are limited in their application because of imprecision and the time consumed for each procedure. Movement by the patient will lead to positioning errors with any system and the necessity for repeating the procedure. Patient motion is much more likely with long procedure times. The use of rigid guides makes it difficult to test for deflection of flexible needles and necessitates sterilization of such equipment. Lateral angular guidance with the prior art techniques is precise, but limited to the plane of the scan. Longitudinal angular guidance is not precise, involving a great deal of estimation, and there is no prior art provision for guidance at compound angles.

SUMMARY OF THE INVENTION

An object of the present invention is to provide a three-dimensional light guidance system for invasive procedures which is equally accurate and easy to use in any direction.

Another object is to provide a system which indicates both point of entry and direction of travel of the invasive instrument.

A further object is to provide a system in which the accuracy can be easily checked and any deflection of the invasive instrument promptly recognized.

The above objects are realized in the present invention by the provision of a light system for producing a line in space above the patient to indicate both the point of entry and the path for an invasive instrument to reach the lesion or target. The guidance system is based upon the principle that the intersection of two planes defines a line. The planes are defined by narrow rotatable light beams positioned in such a manner that the axes about which they are rotated may be positioned to intersect at the target and about these axes the light beams may be rotated to define the best path to that target. The placement of the invasive instrument can be quickly checked against the light beams during insertion and corrections made as required.

BRIEF DESCRIPTION OF THE DRAWINGS

Other objects and features of the present invention will be apparent to those skilled in the art from the following detailed description taken in combination with the attached drawings in which.

DETAILED DESCRIPTION OF THE DRAWINGS

The present invention avoids the disadvantages of the prior art techniques by provision of a light guidance system which provides precise direction as to point of entry and path of insertion of an invasive instrument. The present system provides guidance along the entire path of insertion of the instrument allowing correction in process, thus materially increasing the incidence of first-time correct placement while reducing the percentage of repeat procedures along with the average time of placement.

Figure 1:
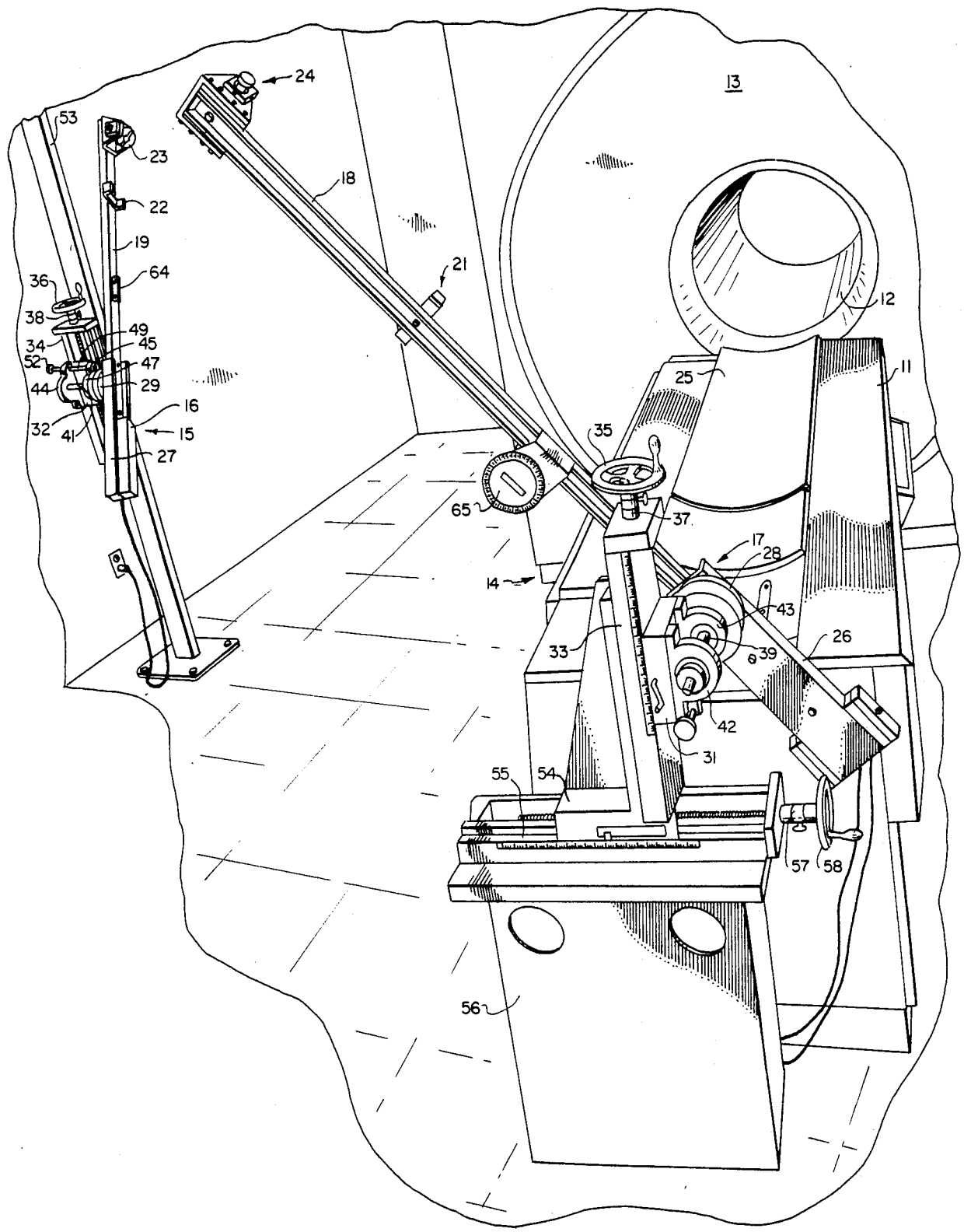
FIG. 1 is a perspective view of a light localizer system according to the present invention in conjunction with a C.T. scanner and table.

Referring to FIG. 1 of the drawing, a C.T. table 11 is positioned adjacent the opening 12 of a C.T. scanner 13. A light localizer 14 is mounted adjacent the end of the table 11 removed from the scanner 13 and a generally similar light localizer 15 is mounted at one side of the table and spaced therefrom. Each localizer is provided with a light source such as a laser 16 and 17 secured to the lower end of a pivotable arm 18 and 19. The light beam from each source is converted into a thin plane of light by passage through a cylindrical lens 21 and 22. A mirror 23 and 24 is mounted at the end of each arm to reflect the light onto the patient. Each mirror is mounted for adjustment relative to the supporting arm 18 and 19, so that the narrow planar beam of projected light can be directed precisely onto the patient and sliding cradle 25 of the table 11 in proximity to the scanner 13.

Figure 2:
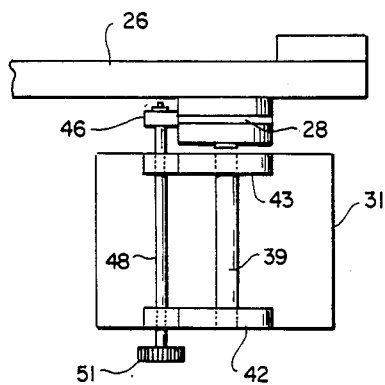
FIG. 2 is an elevational view at an enlarged scale of the vertical saddle block of FIG. 1.

The lower end of each arm 18 and 19 is enlarged to form a flat plate 26 and 27 which serves as a convenient mounting surface for the light source, counter weights, switches, etc. Each arm is pivotally mounted on the saddle block 31 and 32 of a vertical feed table 33 and 34, so that the axes of rotation of each light beam can be elevated or depressed and rotated through approximately 180 degrees. Each feed table 33 and 34 includes an adjusting wheel 35 and 36 and lead screw 37 and 38 which is threadedly engaged with the saddle block 31 and 32. Each arm 18 and 19 is supported on the feed table by means of a shaft 39 and 41 journalled in pillow blocks 42, 43 and 44, 45 which are secured to the saddle blocks 31 and 32. As shown in FIG. 2, each rotational assembly is provided with a brake assembly which includes a disc 28, 29 affixed to shaft 39, 41. A pair of caliper plates 46, 47 straddle the edge of each disc and are each connected to a rod 48, 49 which is journalled in the saddle block. A knob 51, 52 on the end of each rod allows rotation of the rod to draw the caliper plates of each pair together to squeeze the edge of the associated disk and prevent drift of the assembly after it is properly positioned.

Feed table 34 of light localizer 15 is secured to a rigid post 53 which is located near the C.T. scanner 13 and spaced from the table 11. Feed table 33 of light localizer 14 is mounted on the saddle block 54 of a horizontal feed table 55 which is supported on a heavy base 56. The arm 18 is thus mounted for movement horizontally and vertically relative to the table 11. The feed table 55 includes a lead screw 57 threaded into the saddle block 54 and an adjusting wheel 58 for rotating the lead screw.

With a patient lying on cradle 25, the cradle can be moved axially on the table into the opening 12 to position the patient within the scanner 13. The lesion is located and the location within it to become the target of the instrumental passage is established from the C.T. images in vertical and longitudinal planes. The overlying structures and organs are located and a safe path to the lesion is determined. The shafts 39 and 41 of the light localizers are then positioned such that the extended axes of the shafts intersect at the target. This is accomplished by adjusting the vertical positions of the saddle blocks 31, 32 with the adjusting wheels 35, 36, adjusting the horizontal position of the saddle block 31 with adjusting wheel 58 and adjusting the position of the patient relative to saddle block 32 by sliding the cradle 25 axially of the table. The angulation of the path in the transverse and longitudinal planes is computed and the arm 18, 19 of each localizer is rotated about its associated shaft 39, 41 to the desired angle. Each arm is then clamped in position by means of the associated brake assembly.

Figure 3:
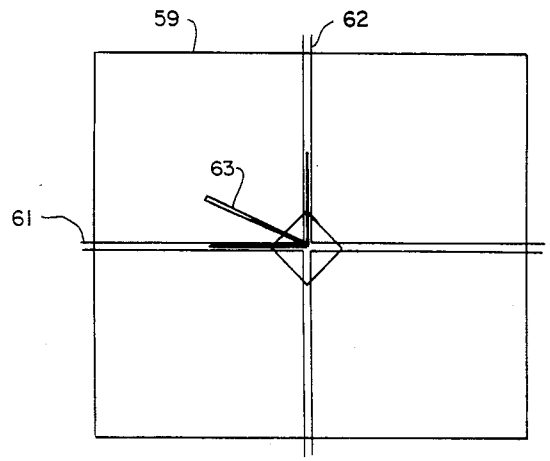
FIG. 3 is a perspective view illustrating the method of placement of an invasive instrument with the apparatus of FIG. 1.

The beams from light sources 16 and 17 define planes which intersect over the patient and form a line lying on the computed path of the invasive instrument. The line begins at the entry point and extends into the space above the patient. Guidance for insertion of the instrument is provided by placing the point of the instrument on the entry point and then pivoting the instrument about this point until the instrument axis is positioned in the line. This is accomplished, as indicated in FIG. 3, by placing a card 59 on the patient adjacent the entry point such that both light beams fall on the card as shown at 61 and 62. When the point of the instrument 63 is positioned on the entry point, the shadow of the instrument is cast in two directions and likewise falls on the card. The instrument is then maneuvered until the shadow falls in both light beams simultaneously. Pressure is then applied to the instrument to penetrate the skin and insert it along the computed path. The accuracy of placement can be ascertained by releasing the instrument and verifying that the shadow continues to fall in both beams. The depth of placement can be easily determined from the length of the instrument remaining above the skin surface.

The present system is illustrated in connection with one pair of light localizers 14 and 15. However, if desired, a second pair of light localizers similar to 14 and 15 could be positioned at the end and side of the C. T. table 11 opposite localizers 14 and 15. Alternatively, to avoid the expense of a second pair of light localizers, a system of mirrors can be provided on the scanner 13 or a support behind it and on a support opposite post 53 to reflect the light beams from localizers 14 and 15 back onto the patient.

While a card such as 59 is illustrated in FIG. 3, it may not be necessary in many instances since the shadow of the instrument may be seen on the patient's skin, the sterile drapings or the operator's hand. The path for the instrument may be computed by the operator or the software associated with the C. T. scanner can be modified to compute the angles and depth directly from the information developed from the scan. In this regard, the present system is useful with computed tomography, but is also applicable to other imaging systems which provide anatomic visualizations with transverse, vertical, and longitudinal localizations.

Figure 4:
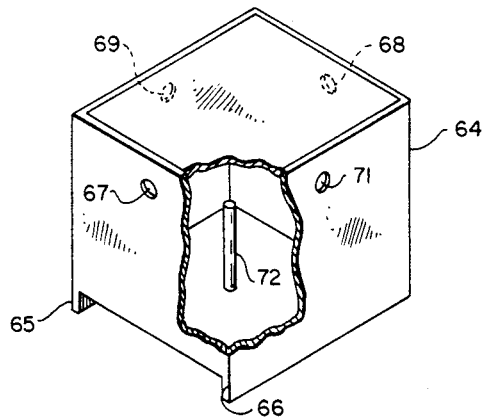
FIG. 4 is a perspective view of an alignment accessory for use with the present system.

Referring to FIG. 4 of the drawing an alignment accessory is illustrated to facilitate initial alignment of the guidance and after installation to check for continued accuracy of alignment. The accessory consists of a transparent box 64 with depending flanges 65, 66 to locate and maintain precise position of the box on the cradle 25. Pairs of marks or openings 67, 68 and 69, 71 are provided in opposite surfaces of the box such that the axis through each pair is perpendicular to the axis through the other pair. The guidance devices (light localizers) are so installed that the extended axes of their shafts 39, 41 pass through the centers of the marks or openings. The extended axis can be determined by rotating the arm 18 or 19 and locating the point on the light beam which does not move. When the extended axis is located each guidance device is positioned such that the extended axis falls in the center of each mark or opening of the associated pair. If desired, a telescopic sight may be mounted in the center of each shaft 39, 41 and alignment achieved by visual observation. An additional target 72 is mounted in the center of the box to check both beam positions simultaneously.

What is claimed is:

1. A method of providing accurate placement and guidance of an elongate needle instrument, such as a biopsy needle, in percutaneous invasive procedures in which the instrument is inserted axially into a patient's body to pierce a tartget zone within the patient's body, said method comprising generating a first planar beam of light above the patient such that the plane of said first planar beam passes through the target zone within the patient's body;

generating a second planar beam of light above the patient such that the plane of said second planar beam intersects the plane of said first planar beam to form a line of intersection and in addition also passes through the target zone within the patient's body;

placing the leading point of of the instrument on the body of the patient at the point of intersection of the first and second planar beams of light on the patient's body;

aligning the instrument within the plane if each planar beam of light such that the axis of the instrument coincides with the line of intersection of the first and second planar beams of light; and inserting the aligned instrument into the patient's body while maintaining the alignment of the instrument along the line of intersection of the first and second planar beams of light.

* * * * *